(12) United States Patent
Li

(10) Patent No.: US 8,859,730 B2
(45) Date of Patent: Oct. 14, 2014

(54) NATIVE CHEMICAL LIGATION AT SERINE AND THREONINE SITES

(76) Inventor: Xuechen Li, Hong Kong (CN)

( * ) Notice: Subject to any disclaimer, the term of this patent is extended or adjusted under 35 U.S.C. 154(b) by 157 days.

(21) Appl. No.: 13/389,202

(22) PCT Filed: Aug. 12, 2009

(86) PCT No.: PCT/CN2009/073204
§ 371 (c)(1),
(2), (4) Date: Feb. 6, 2012

(87) PCT Pub. No.: WO2011/017837
PCT Pub. Date: Feb. 17, 2011

(65) Prior Publication Data
US 2012/0253011 A1    Oct. 4, 2012

(51) Int. Cl.
| | |
|---|---|
| C07K 2/00 | (2006.01) |
| C07K 1/00 | (2006.01) |
| C07K 1/107 | (2006.01) |
| C07K 5/103 | (2006.01) |
| C07K 5/062 | (2006.01) |
| C07K 5/083 | (2006.01) |
| C07K 7/06 | (2006.01) |
| C07K 14/00 | (2006.01) |
| C07K 5/078 | (2006.01) |
| C07K 5/097 | (2006.01) |

(52) U.S. Cl.
CPC ............... *C07K 1/1075* (2013.01); *C07K 5/101* (2013.01); *C07K 5/06052* (2013.01); *C07K 5/0808* (2013.01); *C07K 7/06* (2013.01); *C07K 14/001* (2013.01); *C07K 5/06165* (2013.01); *C07K 5/0823* (2013.01)
USPC ............................ 530/333; 530/300; 530/339

(58) Field of Classification Search
USPC .......................................................... 530/333
See application file for complete search history.

(56) References Cited

FOREIGN PATENT DOCUMENTS

WO          0220557 A1    3/2002

OTHER PUBLICATIONS

Coltart. Tetrahedron (2000) 56, 3449-3491.*
Band et al., Angew. Chem. Int. Ed. (2004) 43, 2534-2538.*
Villain et al., Chemistry & Biology (2001) 8, 673-679.*
Okamoto, Ryo, et al., "Uncovering a latent ligation site for glycopeptide synthesis", Angewandte Chemie, International Edition, 2008, vol. 47, No. 29, pp. 5402-5406.
Offer, John, et al., "Extending Synthetic Access to Proteins with a Removable Acyl Transfer Auxiliary", J. Am. Chem. Soc., 2002, vol. 124, pp. 4642-4646.
First Office Action, dated Mar. 12, 2013, issued by the State Intellectual Property Office of the People's Republic of China in Application No. CN2009801607269 for "Native Chemical Ligation at Serine and Theonine Sites".

* cited by examiner

*Primary Examiner* — Karlheinz R Skowronek
*Assistant Examiner* — Catherine Mader
(74) *Attorney, Agent, or Firm* — David A. Farah; Sheldon Mak & Anderson PC

(57) ABSTRACT

A chemoselective chemical ligation method is disclosed. The method joins two peptide segments efficiently to produce a larger peptide or protein, by generating a natural peptide bond (Xaa-Ser and Xaa-Thr) at the ligation site (Xaa represents any 5 amino acid). The method requires two steps (FIG. 1 (*a*)): a) reacting the starting peptide(s) to form an acetal intermediate with an acetal group at the ligation site; b) converting said acetal intermediate to a desired peptide or protein with said natural peptide bond.

20 Claims, 7 Drawing Sheets

(A)

R₁ = Peptide1, R₂ = Peptide2; X = O, or S, or Se; R' = H or Me; Y = substituent (B)

R₁ = Peptide1, and R₂ = Peptide2; R' = H or Me

| Entry | $R_1$ | A% (conversion) at 30 min | A% (conversion) at 5 h | B | % |
|---|---|---|---|---|---|
| 1 | Ala | 88 | 100 | Ala-Ser | 95 |
| 2 | Val | >80 | 100 | Val-Ser | 98 |
| 3 | Pro | 71 | 100 | Pro-Ser | 99 |
| 4 | Ile | 10 | 55 | Ile-Ser | N/A |
| 5 | Val-Thr | 76 | 100 | Val-Thr-Ser | 97 |

| Entry | $R_1$ | A% (conversion) at 30 min | A% (conversion) at 5 h | B | % |
|---|---|---|---|---|---|
| 6 | Ala | 76 | 100 | Ala-Thr-Phe | 99 |
| 7 | Val | 73 | 100 | Val-Thr-Phe | 96 |
| 8 | Pro | 75 | 100 | Pro-Thr-Phe | 98 |
| 9 | Ile | >80 | 100 | Ile-Thr-Phe | 98 |
| 10 | Val-Thr | 74 | 100 | Val-Thr-Thr-Phe | 92 |

A) Crude reaction mixture from the ligation between Fmoc-Val-Thr-salicylaldehyde ester and H-Ser-OBn; B) Standard Fmoc-Val-Thr(D)-Ser-OBn doped with 5% above crude reaction mixture; C) Standard Fmoc-Val-Thr(D)-Ser-OBn doped with 60% crude reaction mixture.

1) Ala-Ser

2) Val-Ser

3) Ile-Ser

1) Ala-Thr-Phe

2) Val-Thr-Phe

3) Ile-Thr-Phe

UV and MS traces from LCMS analysis of the three-segment-coupled product after purification.
ESI-MS calcd for $C_{154}H_{227}N_{46}O_{46}S_3$ $[M+3H]^{3+}$ 1184.2, found : 1184.6

NATIVE CHEMICAL LIGATION AT SERINE AND THREONINE SITES

TECHNICAL FIELD OF INVENTION

The invention relates to methods and acetal intermediates for chemically ligating two peptide segments end to end with a natural peptide bond. More particularly, the invention relates to methods and acetal intermediates for chemical ligation wherein N-terminal serine or threonine of a first starting peptide condenses rapidly with a second starting peptide with a C-terminal aryl aldehyde ester to form an acetal intermediate which is readily converted into the ligation product with a natural peptide bond as Xaa-Ser/Thr at the ligation site (Xaa represents any amino acid).

BACKGROUND OF THE INVENTION

In addition to recombinant DNA technology to provide proteins, the chemical synthesis of proteins has dramatically contributed to the exploration of the relationship of protein structure to function. Moreover, with the rapid emergence of peptides of middle size (between 20 and 100 amino acids) as therapeutics, synthetic peptide chemistry has been flourishing more than ever. Merrifield's linear solid phase peptide synthesis (SPPS) has provided a general tool to prepare polypeptides. However, to chemically synthesize a large polypeptide (>50 amino acids) using linear solid phase peptide synthesis is very costly and sometimes even impossible. Thus, the method to achieve a convergent synthesis of polypeptides becomes critical. Using less or no protecting groups and the efficiency of the coupling step are the critical issues in the development of a convergent synthesis. Use of unprotected peptides for chemical manipulation circumvents the difficulty inherent to classical peptide coupling reactions derived from limited solubility, thus increasing the coupling yield, and leading to the easy purification and characterization. The key issue to develop peptide coupling methods using unprotected peptide segments is the availability of a chemoselective reaction to specifically and unambiguously join peptides through C-terminus of a peptide and N-terminus of a second peptide. Using a chemoselective reaction to join two peptide segments through formation of an unnatural (i.e. non-peptide) backbone structure at the ligation site has permitted the facile preparation of a wide range of backbone-modified artificial peptides and proteins. However, in order to achieve native chemical ligation (ligating two peptide segments through natural peptide bonds), chemical method is very limited. Using unprotected peptides, forming natural peptidic bonds at the ligation site and resulting in no or little epimerization of the formed peptide bond are characteristics of a practical native chemical ligation.

Clearly, cysteine based native chemical ligation (NCL), developed by Kent and coworkers, meets these criteria, and it has become no doubt the most powerful method in synthetic peptide chemistry (Dawson P. E.; Muir, T. R.; Clarklewis, I.; Kent, S. B. H. *Science,* 1994, 266, 776-779, "synthesis of proteins by native chemical ligation"). This method enables a convergent synthesis of larger size peptides and even proteins. The repertoire of NCL has widely been expanded to various aspects in chemistry and biology over the past 15 years. Cysteine based NCL features a thio capture between an N-terminal cysteine and a C-terminal thioester, as a transthioesterification step which is highly chemoselective, followed by a rapid S→N acyl transfer to afford a natural Xaa-Cys peptidic linkage (Xaa represents any amino acid). Its efficiency, easy operation and chemoselectivity (in presence of any unprotected amino acid) are very attractive to its users/practitioners, thus cysteine based NCL has been widely used for chemically synthesizing many proteins (>100 amino acids). That the cysteine based NCL achieves the chemoselectivity lies in that the N-terminus cysteine can differentiate itself from other inner unprotected amino acid functional groups with its bifunctionalities: a 1,2-mercapto-amine. Moreover, the capture-rearrangement chemical ligation does not involve activating the carboxyl group, thus native chemical ligation overcomes the racemerization problem of the conventional segment condensation method.

However, the rare presence of the cysteine residue (1.4% content in proteins) has limited the utility of the above NCL. To address this issue, people have extensively searched for alternative native chemical ligation methods at other amino acid sites. By far, all alternatives recently developed follow the line of cysteine based native chemical ligation, relying on the thio-capture-rearrangement strategy. Many efforts are focused on introducing β or γ-thio group into natural amino acids. After the cysteine-like native chemical ligation, the thio group of the ligated product is removed to achieve a ligation at the corresponding amino acid. Other efforts are directed to the development of chemical manipulation conditions to convert the cysteine-NCL product into other forms of amino acids, i.e. desulfurization of cysteine to give alanine. All these methods have expanded the arsenal for peptide/protein ligation and have been used to prepare various (glyco)peptide/proteins at a very complicated level (Offer, J.; Boddy, C. N. C.; Dawson, P. E. *J. Am. Chem. Soc.,* 2002, 124, 4642-4646, "Extending synthetic access to proteins with a removable acyl transfer auxiliary"). However, the practice of these methods requires either sophisticated chemistry or syntheses of unnatural amino acids, therefore, they are not as generally used as cysteine-based NCL. Moreover, these methods all affect unprotected cysteine residues in addition to the cysteine residue at the ligation site. The chemoselective ligation using user-friendly conditions at other amino acid sites has yet to be discovered.

SUMMARY

The present invention relates to a method for ligating two peptides by generating a natural peptide linkage, as another Native Chemical Ligation (NCL). The well-known cysteine based NCL relies on using a cysteine residue at the N-terminus of a peptide segment and a thioester as the C-terminus of another peptide segment to generate the Xaa-Cys linked peptide. Differently, the method of the present invention uses a serine or threonine at the N-terminus of a peptide segment and an aryl aldehyde ester (e.g. salicylaldehyde ester) as the C-terminus of another peptide segment to generate the Xaa-Ser or Xaa-Thr linked product (Xaa represents any amino acid), to achieve serine and threonine based native chemical ligation.

One embodiment of the invention provides a method of serine and threonine-based native chemical ligation, which features using unprotected peptide segments, leading to no epimerization, easy operations, rapid conversion and forming natural peptide bonds as Xaa-Ser and Xaa-Thr at the ligation site. FIG. 1 demonstrates the principle of this Ser/Thr native chemical ligation, as exemplified by using C-terminal salicylaldehyde ester. The first step is the chemoselective reaction of a peptide having a salicylaldehyde ester at the C-terminus with another peptide segment possessing an N-terminal serine or threonine residue to give an isolatable intermediate with a N,O-benzylidene acetal moiety at the ligation site. Without purification, the N,O-benzylidene acetal intermediate is converted to the target full-length polypeptide product with a natural peptidic bond at the ligation site. The two steps are carried out in the same flask without purifying the intermediate. Except the salicylaldehyde ester, the aryl ester at the C-terminus can expand to other aromatic or hetero-aromatic systems, wherein the hetero-atom in the hetero-aromatic systems is at least one atom selecting from N, O and S. For instance, the phenyl ring of the salicylaldehyde also can be replaced with a six-member or five-member (hetero)aromatic ring selecting from pyridine, pyrimidine, pyridazine, pyrrole, furan, thiophene, imidazole, pyrazole, oxazole, isoxazole and thiazole. When these aryl esters are used at the C-terminus, the coupled products possess corresponding acetal groups at the ligation site.

The invention provides an applicable method for ligating a first oligopeptide end with a second oligopeptide end, or two ends of the same oligopeptide, for producing an oligopeptide product or a circular peptide with the natural peptidic bond at the ligation site. The first oligopeptide includes a C-terminal salicylaldehyde ester. The second oligopeptide includes an N-terminal serine or threonine. The first and second oligopeptides are admixed in a reaction solution without using any external catalyst/reagent. After the completion of the reaction (2-10 hours for any tested case), the solvent is removed and the residue is treated for the final conversion (less than 10 minutes) to give a natural target full-length polypeptide.

Another aspect of the invention is directed to an oligopeptide intermediate which comprises a first starting peptide segment having a C-terminal salicylaldehyde ester, a second starting peptide segment having a serine or threonine, and an adduct with N,O-benzylidene acetal unit which links the C-segment and N-segment. The N,O-benzylidene adduct is rapidly converted into a peptidic bond linking the first and second starting peptide segments end to end.

The invention stated herein is very chemoselective without protecting any amino acid for the coupling of two peptide segments. Another characteristic of the invention is the rapid coupling of the two peptide segments, even for very hindered amino acids at the C-terminus, such as valine, proline, isoleucine, and threonine, as shown in FIG. 3. These β-branched amino acids when used at the C-terminus dramatically retard the coupling process, thus most known ligation methods require a prolonged time (>48 hours) for completion at these amino acid sites or are limited to less hindered amino acids at the C-terminal site. Under the condition of the present invention, the ligation involving these hindered amino acids is still efficient and rapid, resulting in 100% conversion in less than 5 hours for very hindered amino acids.

Another aspect of the invention is directed to a method where joining two peptide segments generates a natural peptidic bond at the ligation site in an epimerization-free manner. Avoiding epimerization is a big challenge under the conventional peptide coupling condition. Using imine-capture-acyl transfer from 1,2-hydroxyl-amine bifunctionality of serine and threonine to from amide bonds does not involve activating the carboxyl group of C-terminal end, thus minimizing the tendency of racemerization.

A prominent aspect of this invention is to provide a native chemical ligation method using user-friendly conditions, without consulting any sophisticated chemistry and special care. The method of the present invention is easily operative and the working condition is well suitable for peptide chemistry.

Tam et al discloses a method for ligation of a C-terminal glycolaldehyde peptide with another peptide containing a Cys, Thr or Ser residue at the N-terminus to furnish a pseudoproline structure (Liu, C. F.; Tam, J. P. *J. Am. Chem. Soc.*, 1994, 116, 4149-4153, "Chemical ligation approach to form a peptide-bond between unprotected segments-concept and model studies"). Using this method, artificial proteins with pseudoproline structure (thiazolidine or oxazolidine) are prepared by ligating two peptide segments to mimic the proline-containing protein structure at the corresponding position. However, a limitation of the Tam approach is the reaction rate. The method did achieve great chemoselectivity, but the ligation was extremely slow when threonine or serine is used at the N-terminus (less than 84% conversion at 45 h on the model system between glycine and serine). More importantly, the limitation of the Tam approach is that the conversion from the pseudoproline into natural peptidic bonds has not been achieved. Thus, the ligated product does not contain a natural peptidic bond. Therefore, Tam approach is not a native chemical ligation and is unable to provide a convergent synthesis of a protein or peptide with the natural peptide sequence.

The method of the invention facilitates the chemical synthesis of proteins and large oligopeptides. Serine and threonine together represent 12.7% content in proteins, almost 10 times more than cysteine, thus the serine and threonine based chemoselective ligation methods should find greater applications in synthetic peptide chemistry and bioconjugation chemistry. It can dramatically decrease the production cost of therapeutic peptides of middle size (between 20 and 100 amino acids). Many peptide drugs contain inner serine and threonine residues. Using linear SPPS to prepare small peptide segments (<20 amino acids), together with applying the serine and threonine based native chemical ligation of the present invention for a convergent synthesis will potentially facilitate the massive production of these peptide drugs in a cost-less manner. The method of the present invention can also be used to prepare cyclic peptides, by introducing the C-terminal aryl aldehyde ester and N-terminal serine or threonine on the same starting peptide. In addition, the method developed in this application will make N-linked glycoproteins readily available for chemical synthesis, because all N-linked glycoproteins have serine or threonine residues. Furthermore, an N-terminal serine or threonine residue can be expressed to a protein of interest by standard recDNA means. It could be reacted with the synthetic small molecule or peptide containing a salicylaldehyde ester using the native chemical ligation described here to label the protein of interest or to generate a "hybrid" protein complex.

BRIEF DESCRIPTION OF DRAWING

FIG. 1(B) is a chemical formula representation of the mechanism of the acyl transfer reaction step of the method of the present invention.

FIG. 2 (B) LCMS profile of chemoselectivities as shown on FIG. 2, A.

DETAILED DESCRIPTION

Figure 1:
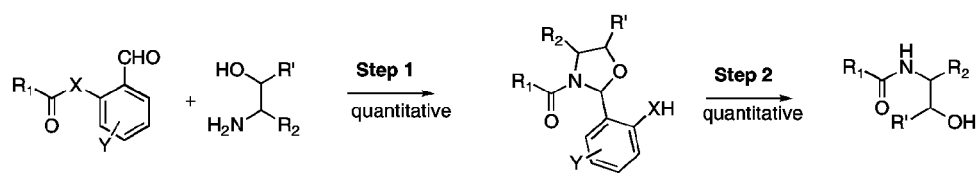
FIG. 1 (A) illustrates the overall principle of Ser/Thr-based native chemical ligation.
Figure 1:
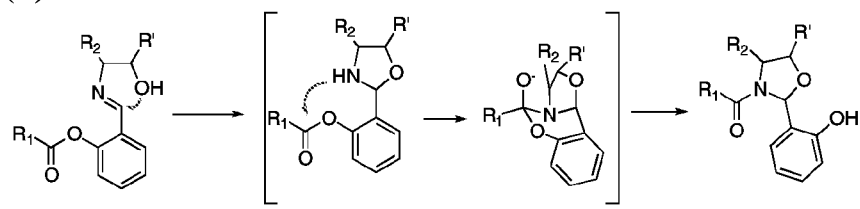

The present invention provides a method of chemically ligating a first starting peptide segment to a second starting peptide segment. The method uses an aryl aldehyde ester (e.g. salicylaldehyde ester) as the C-terminal partner and an either serine or threonine as the N-terminal partner to produce a larger peptide with Xaa-Ser/Thr peptide linkage at the ligation site (Xaa represents any amino acid).

In the method, the aryl aldehyde ester (e.g. salicylaldehyde ester) of the C-terminal peptide is crucial in the development of serine and threonine based native chemical ligation. Using a C-terminal glycolaldehyde ester peptide has been reported to react with a serine or threonine peptide, but the reaction rate is extremely slow (i.e. less than 84% conversion after 45 hours on the model system between glycine and serine). However, the aryl aldehyde ester, such as a salicylaldehyde ester, at the C-terminus dramatically expedites the reaction rate of the coupling step, for instance, a quantitative conversion is achieved for all tested amino acids in less than 5 hours. More importantly, the N,O-benzylidene acetal generated after coupling is easily removable under mild conditions (i.e. acidic conditions) to afford natural peptide bonds at the ligation site, as achieved in native chemical ligation. The aryl aldehyde ester is O-ester, S-ester, or Se-ester. The reactivity of the coupling step and removal step can be further tuned by introducing substitution on the phenyl ring of the salicylaldehyde ester, such as halide, alkyl, alkoxyl, amide, azido and nitro. The installment of a nitro group will enable the removal of the N, O-benzylidene acetal group under UV light. The phenyl ring of the C-terminal salicylaldehyde ester can also be replaced with other (hetero-)aromatic systems, wherein the hetero-atom in the hetero-aromatic systems is at least one atom selecting from N, O and S, such as pyridine, pyrimidine, pyridazine, pyrrole, furan, thiophene, imidazole, pyrazole, oxazole, isoxazole and thiazole.

In the method, the N-terminal peptide possess either serine or threonine residue. They can be used in the salt form. Serine and threonine together represent 12.7% content in proteins, thus they can be easily found in the synthetic target protein or peptide of interest.

The method of the present invention virtually has two steps. The first step involves admixing the N-terminal peptide having either serine and threonine and the C-terminal peptide having a salicylaldehyde ester in the reaction solvent. A mixture of pyridine and acetic acid (1:1, mol/mol) is found to give the best yield. Herein, the amine group of the N-terminal serine or threonine reversibly reacts with the aldehyde group of the salicylaldehyde ester to form an imine, followed by the cyclization from the α-hydroxyl group of the N-terminal serine or threonine. Next, a 1,5 O→N acyl transfer affords a stable N, O-benzylidene acetal intermediate (when other types of aryl esters are used at the C-terminus, the corresponding acetal intermediate is generated). The second step involves using acid conditions to remove the N,O-benzylidene acetal group to form native peptide bonds. Herein, after removal of the solvent (pyridine/acetic acid) by lyophilization, the crude N,O-benzylidene acetal intermediate is subjected to a solution mixture of $TFA/H_2O/iPr_3SiH$ to afford the natural peptide bond in less than 5 minutes. This acidic condition is generally used in peptide chemistry. Introducing photoreactive groups onto the phenyl ring of the salicylaldehyde ester, such as nitro, could potentially realize the removal of the N,O-benzylidene acetal under UV light.

The method is highly chemoselective. The ligation proceeds in the presence of any unprotected amino acid and other reactive acyl donors such as a thiophenol ester. The method has two steps (FIG. 1). The first step involves the amino group of N-terminal serine or threonine reacting with the aldehyde group of the C-terminal salicylaldehyde ester. Other nucleophiles like a lysine may also react with the aldehyde group, but the reaction is reversible and unproductive to give a stable product. The coupling step of the method is economic and easily operative without using any external reagent, and results in full conversion over a short time period. The second step features rapid reaction, simple operation and using user-friendly conditions. Both reaction conditions are generally used in peptide chemistry, and thus well compatible with most functionalities in peptides and glycopeptides.

Figure 3:
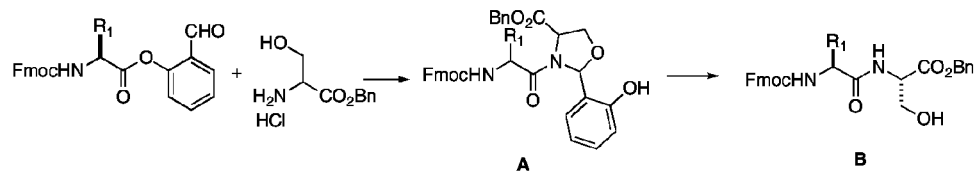
FIG. 3 demonstrates the scope of serine/threonine-based chemical ligation using hindered amino acids.
Figure 3:
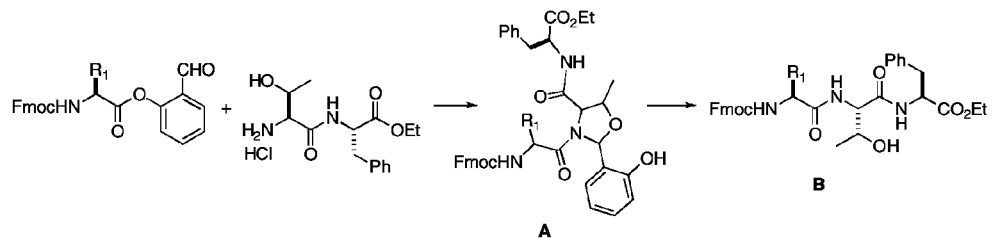

The method of the present invention features, albeit in a two-step sequence, rapid and efficient coupling of two peptide segments, even for very hindered amino acids at the C-terminus, such as valine, proline, isoleucine, and threonine, as shown in FIG. 3. These β-branched amino acids when used at the C-terminus dramatically retard the coupling process under other known ligation conditions (e.g. cysteine-based NCL requires 48 hours), while under the condition of the present invention, the ligation involving these hindered amino acids can complete in less than 5 hours.

Another feature of the method of the present invention is the orthogonality between Ser/Thr based native chemical ligation with Cys based native chemical ligation. The thioester used for Cys-NCL is stable under the condition of the present invention. Thus, Ser/Thr-NCL can be used together with Cys-NCL to achieve a one-pot-three-segment ligation in the direction from the N to the C terminus.

EXAMPLE 1

As a model study, FmocAla with salicylaldehyde ester at the C-terminal was prepared by coupling FmocAla-OH with salicylaldehyde using dicyclohexylcarbodiimide under standard ester formation conditions. A typical procedure for Ser/Thr NCL is as follows: FmocAla-salicylaldehyde ester (3.8 mg, 9.15 μmol) and serine benzyl ester (2.5 mg, 10.8 μmol) are mixed in a solution (183 μl, pyridine/acetic acid, 1:1, mol/1 mol) at a concentration of 0.05 M. The reaction mixture is stirred at room temperature and is monitored by LCMS. After 30 min, a single new product in 80% conversion is observed, corresponding to the N,O-benzylidene acetal adduct. The reaction goes to completion within 2 hours to afford the coupled product with the N, O-benzylidene acetal in between. The N,O-benzylidene acetal adduct can be isolated. NMR spectrum of the N,O-benzylidene adduct appears as two compounds, which is derived from the new generated chiral center. (Fmoc=fluorenylmethyloxycarbonyl, LCMS=liquid chromatography-mass spectrometry, NMR=nuclear magnetic resonance)

On the other path, the crude reaction mixture from the above coupling, after removal of the solvent (pyridine/acetic acid) by lyophilization, is directly subjected to the next step. Treatment with an acidic condition ($TFA/H_2O/Pr_3SiH$, 94/5/1, v/v/v, 1.0 ml) smoothly converts the N,O-benzylidene acetal adduct into a "natural" Ala-Ser dipeptide in quantitative conversion in 4 minutes. Purification by HPLC ($C_{18}$, 50-90%, MeCN (with 0.04% TFA)/$H_2O$ (with 0.05% TFA), 30 min, flow rate 16 ml/min) gives Fmoc-Ala-Ser-OBn dipeptide (4.2 mg, 95%). This acidic condition is generally used in glycopeptides/glycoproteins synthesis. Both steps proceed rapidly and cleanly, without detecting any significant byproduct or hydrolysis product. (TFA=trifluoroacetic acid)

EXAMPLE 2

Figure 2:
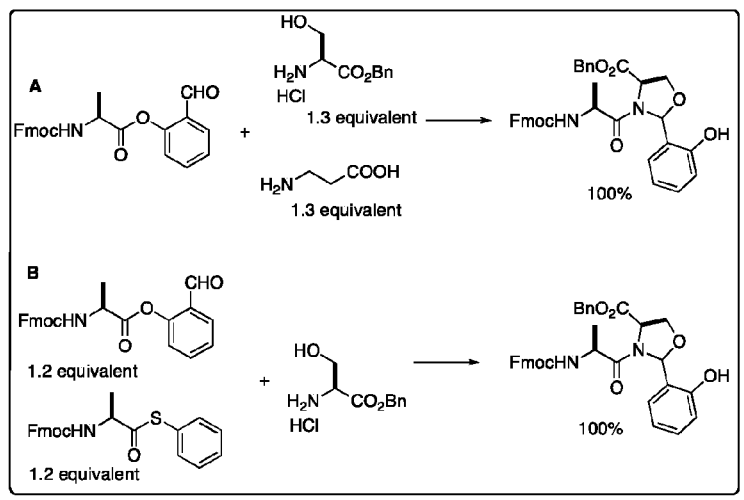
FIG. 2 (A) illustrates the chemoselectivities of the method of the present invention.
Figure 2:
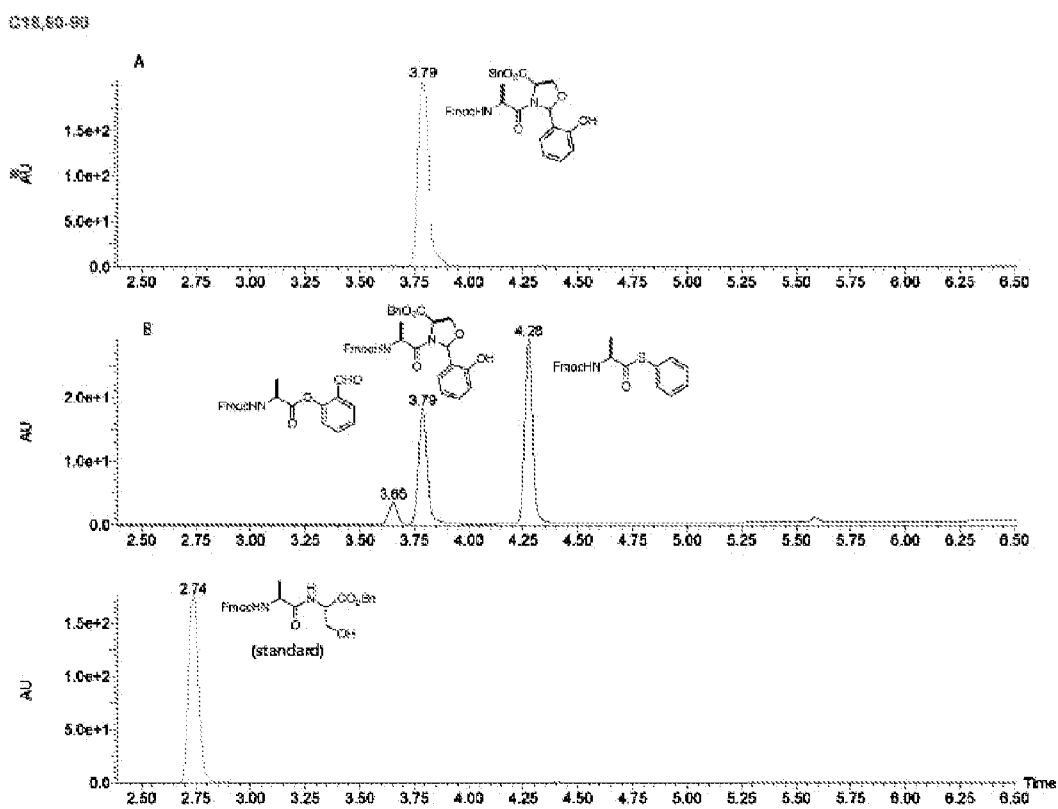

The significant feature of the present method is its chemoselectivity. To demonstrate the chemoselectivity, using the same condition as described above, the Ala-salicylaldehyde ester reacts with a serine derivative in the presence of an unprotected β-alanine. Moreover, the Ala-salicylaldehyde ester reacts with a serine derivative in the presence of an Ala-thiophenol ester. The reaction is monitored by LCMS and the reaction product is determined by ESI (electrospray mass spectrometry). In both cases, a single product of the expected mass as the N,O-benzylidene adduct is observed (FIG. 2). The thiophenol ester is a very reactive acyl donor. It is reported to directly condense with an amine to give an amide bond and readily hydrolyze. Under the condition of the present invention, the thiophenol ester is stable within the reaction time and does not acylate the amino group directly. These results also demonstrate that the nucleophilic amine does not interfere the ligation process.

EXAMPLE 3

Figure 5:
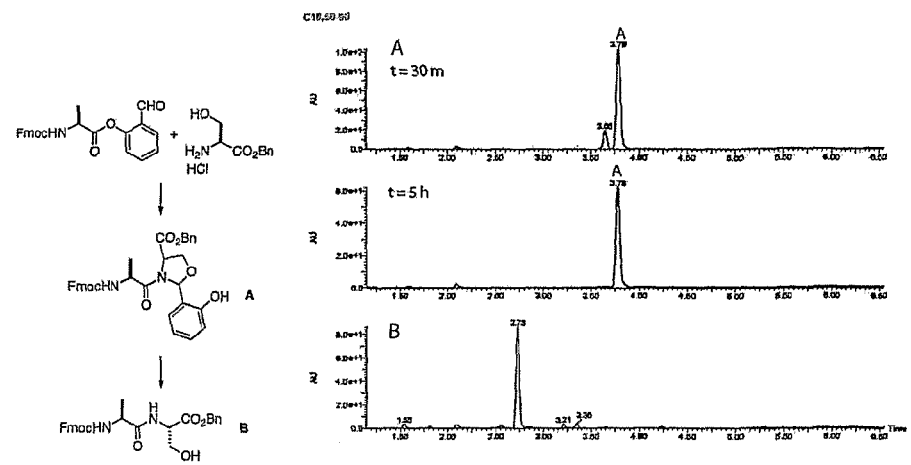
FIG. 5 LCMS profile of serine ligation process.
Figure 5:
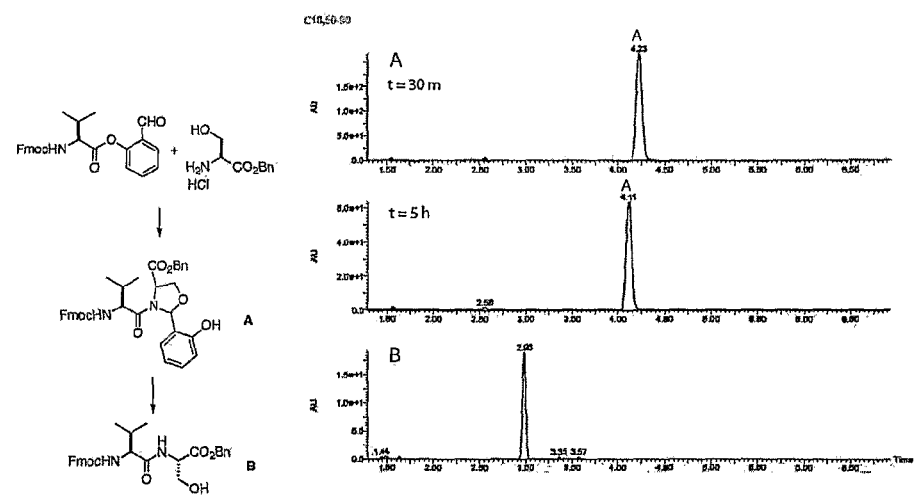
Figure 5:
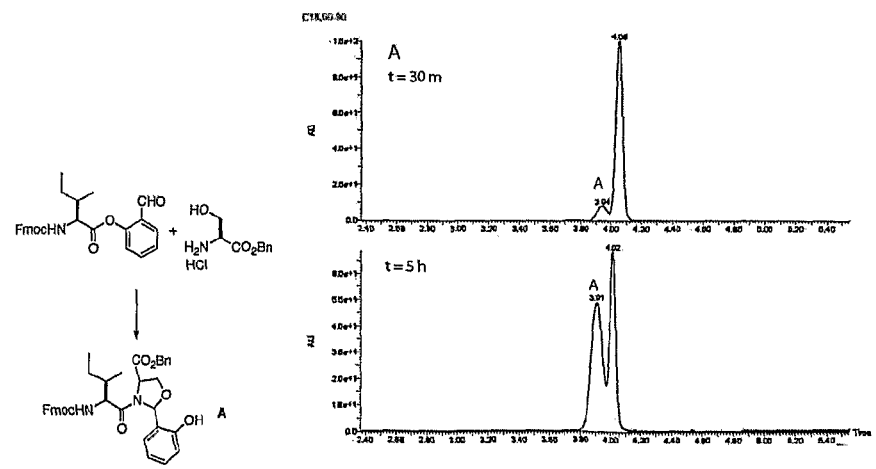

The β-branched amino acids, such as valine, proline, threonine, and isoleucine have been considered as difficult site when used at the C-terminus for chemical ligations. The scope of the serine-based ligation of the present invention is explored with Fmoc-Val-salicylaldehyde ester, Fmoc-Pro-salicylaldehyde ester Fmoc-Ile-salicylaldehyde ester Fmoc-Val-Thr-salicylaldehyde ester coupling with a serine benzyl ester derivative. All ligations are performed at a concentration of 0.05 M, as described in EXAMPLE 1. The reaction is stirred at room temperature and monitored by LCMS. All ligations proceed rapidly and efficiently, resulting in full conversion in less than 5 hours in quantitative conversion for valine, proline and threonine. The exception is that the ligation between isoleucine and serine is rather slow (FIG. 5). After removal of the solvent from the above reactions, the residue is then subjected to TFA/$H_2O$/$iPr_3SiH$ condition. In 5 min, the ligated products in the native peptide form (i.e. Val-Ser, Pro-Ser and Val-Thr-Ser) are obtained (>95%).

EXAMPLE 4

Figure 6:
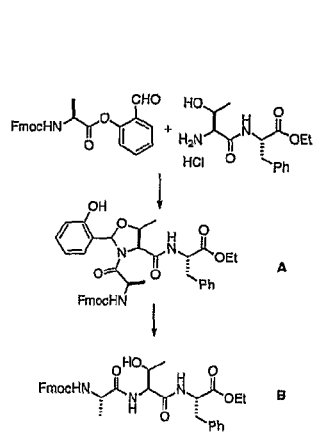
FIG. 6 LCMS profile of threonine ligation process.
Figure 6:
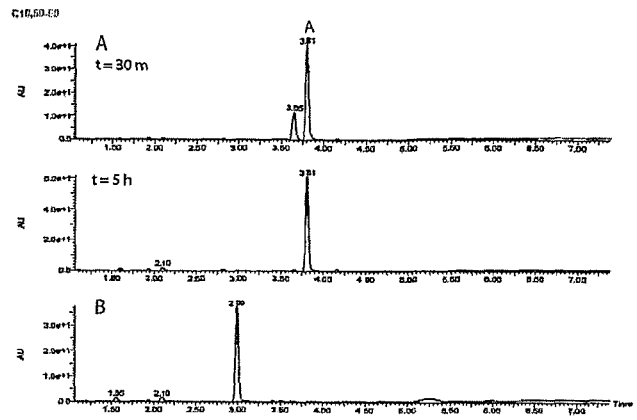
Figure 6:
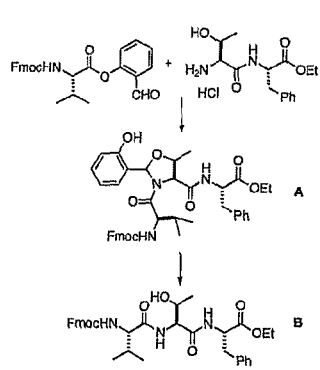
Figure 6:
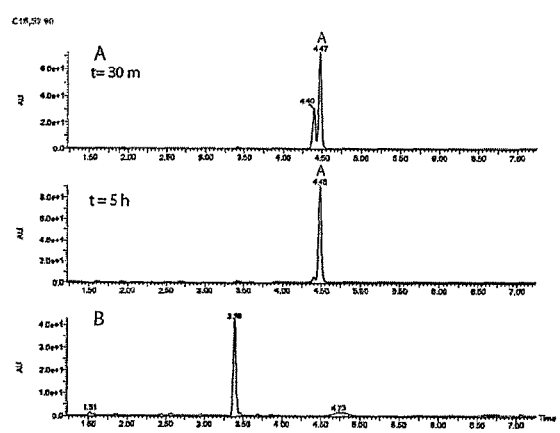
Figure 6:
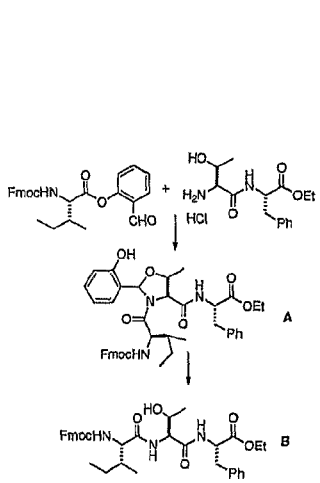
Figure 6:
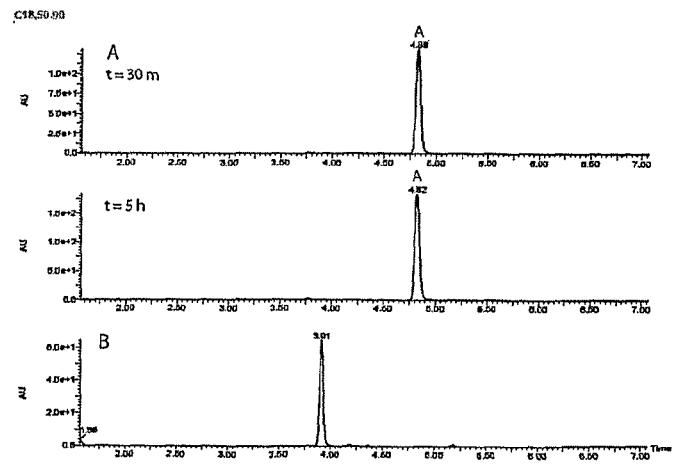

All β-branched amino acids (valine, proline, phreonine and isoleucine) are tested in threonine-based chemical ligation using Fmoc-Val-salicylaldehyde ester, Fmoc-Pro-salicylaldehyde ester, Fmoc-Ile-salicylaldehyde ester, Fmoc-Val-Thr-salicylaldehyde ester coupling with the H-Thr-Phe-OEt dipeptide. All ligations proceed rapidly and efficiently by a two-step sequence to afford tripetides or tetrapeptides in native peptide forms in high yields (>92%) (FIG. 6).

EXAMPLE 5

Figure 4:
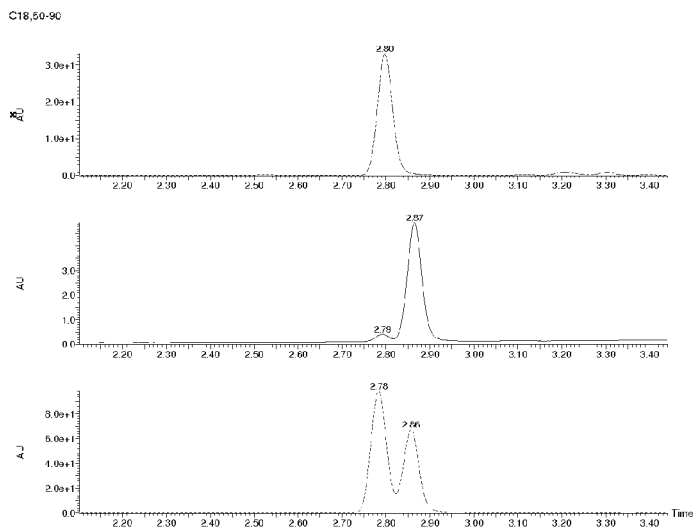
FIG. 4 demonstrates the ligation proceeding without epimerization.

The issue of racemerization is studied using the coupling between a dipeptide Fmoc-Val-Thr-salicylaldehyde ester and a H-Ser-OBn to generate a tripeptide Fmoc-Val-Thr-Ser-OBn. The standard epimer Fmoc-Val-Thr(D)-Ser-OBn is prepared separately as a reference compound, using conventional peptide coupling procedures. As shown in FIG. 4, The product (i.e. Fmoc-Val-Thr-Ser-OBn) from the crude two-step ligation reaction mixture is compared with Fmoc-Val-Thr(D)-Ser-OBn. As shown by LCMS (FIG. 4), the crude coupling reaction does not contain the detectable formation of Fmoc-Val-Thr(D)-Ser-OBn. Therefore, the serine-based chemical ligation does not lead to epimerization at the ligation site.

EXAMPLE 6

The power of this chemical ligation is further demonstrated by a sequential Ser-NCL and Cys-NCL in one-flask reaction. This protocol involves an unprotected peptide possessing a salicylaldehyde ester, an unprotected peptide having serine at the N-terminus and a thiophenol ester at the C-terminus, and an unprotected peptide with an N-terminal cysteine.

The model unprotected peptide with a C-terminal salicylaldehyde ester is prepared as follows: Fmoc-Arg(Phf)-Ala-Ser(t-Bu)-Ile-Thr(t-Bu)-Thr(t-Bu)-Ala-Asp(t-Bu)-Gly-OH is prepared using an automatic solid phase peptide synthesizer employing Fmoc-Gly-NovaSyn® TGT resin and standard Fmoc amino acids. After completion of the synthesis, the resin is treated with a mixture of TFE/$CH_2Cl_2$/AcOH (1/8/1, v/v/v) to give the crude protected peptide. The crude protected peptide (12 mg, 7.5 μmol) and salicylaldehyde (3.9 μl, 37 μmol) and DCC (3.1 mg, 15 μmol) are mixed in anhydrous chloroform (1.0 ml). The reaction mixture is stirred at room temperature for 2 hours and the solvent is blown off by a stream of air. Then the residue was treated with a deprotection mixture (TFA/$H_2O$/PhOH, 3.3 ml/136 μl/160 mg). After stirring at room temperature for 2 hours, the solvent is blown off by a stream of air, and then the peptide is precipitated out by ether, followed by HPLC purification to give the product Fmoc-Arg-Ala-Ser-Ile-Thr-Thr-Ala-Asp-Gly-O-salicylaldehyde ester (5.0 mg, 54%).

The model unprotected peptide having serine at the N-terminus and a thiophenol ester at the C-terminus is prepared as follows: Boc-Ser-Ala-Gln(Trt)-Lys(Boc)-Arg(Pbf)-His(Trt)-Phe-Gly-COOH is prepared using an automatic solid phase peptide synthesizer employing Fmoc-Gly-NovaSyn® TGT resin and standard Fmoc amino acids. After completion of the synthesis, the resin is treated with a mixture of TFE/$CH_2Cl_2$/AcOH (1/8/1, v/v/v) to give the crude protected peptide. The crude protected peptide (23 mg, 12 μmol), an alanine thiopheol ester (3.9 mg, 18 μmol), EDC (3.4 μl, 19 μmol) and HOOBt (1.0 mg, 6.1 μmol) are mixed in anhydrous TFE/chloroform (0.3 ml/0.6 ml). The reaction mixture is stirred at room temperature for 2 hours and the solvent is blown off by a stream of air. Then the residue was treated with a deprotection mixture (TFA/$H_2O$/PhOH/$iPr_3SiH$, 3.3 ml/136 μl/160 mg/60 μl). After stirring at room temperature for 2 hours, the solvent is blown off by a stream of air, and then the peptide is precipitated out by ether, followed by HPLC purification to give the product H-Ser-Ala-Gln-Lys-Arg-His-Phe-Gly-Ala-SPh (7.0 mg, 53%).

The model unprotected peptide with an N-terminal cysteine is prepared as follows: Boc-Cys(S-t-Bu)-His(Trt)-Cys(Acm)-Ser(t-Bu)-Thr-(t-Bu)-Cys(Acm)-Tyr(t-Bu)-Tyr(t-Bu)-His(Trt)-Lys(Boc)-Ser-OH is prepared using an automatic solid phase peptide synthesizer employing Fmoc-Ser(tBu)-NovaSyn® TGT resin and standard Fmoc amino acids. After completion of the synthesis, the resin is treated with a mixture of TFA/$H_2O$ (3.3 ml/136 μl). Then the solvent is blown off by a stream of air, and the peptide is precipitated out by ether, followed by HPLC purification to give the product H-Cys(S-t-Bu)-His-Cys(Acm)-Ser-Thr-Cys(Acm)-Tyr-Tyr-His-Lys-Ser-OH in 70% yield.

Figure 7:
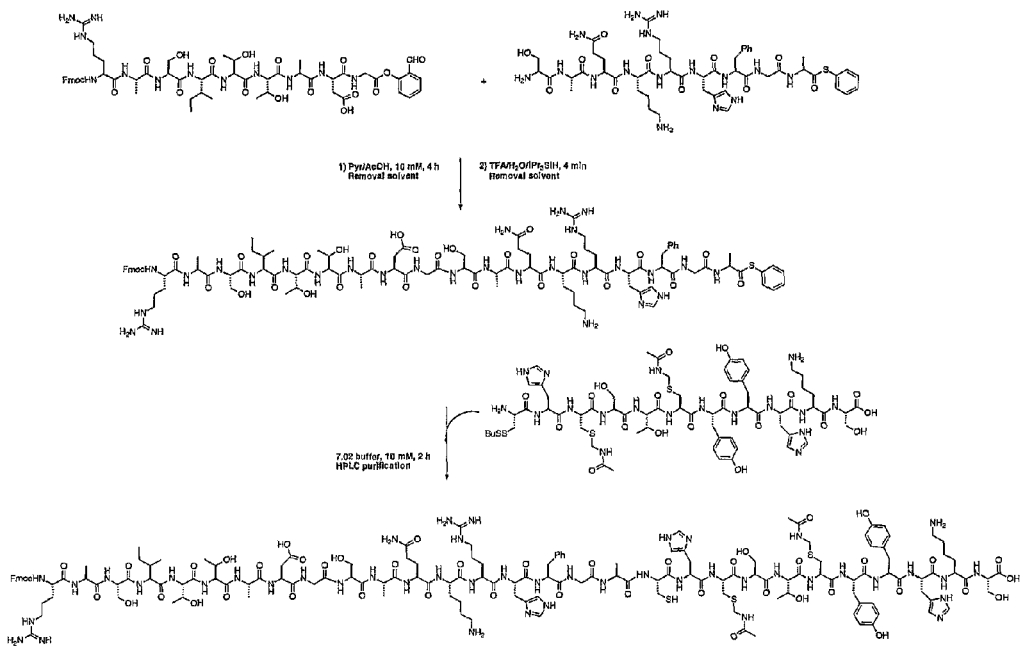
FIG. 7 illustrates a three-component ligation in one flask for assembling multiple fragments from the C to the N terminus.
Figure 7:
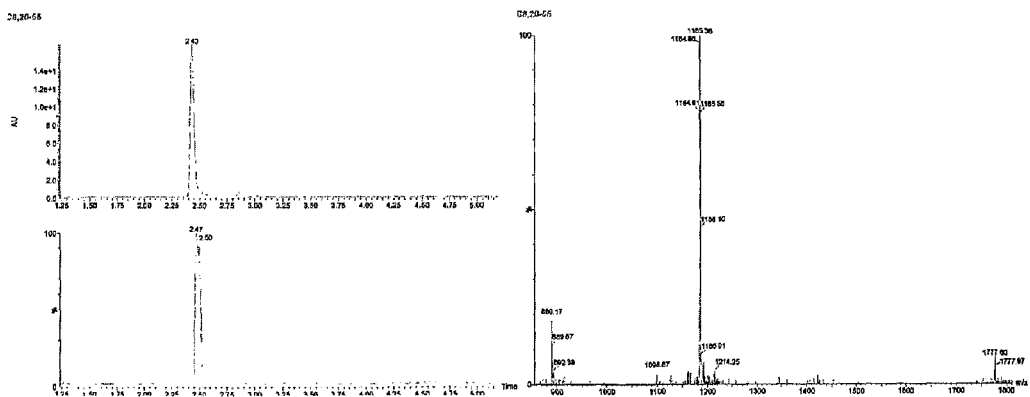

To realize one-pot-three-segment ligation, firstly, Fmoc-Arg-Ala-Ser-Ile-Thr-Thr-Ala-Asp-Gly-O-salicylaldehyde ester (0.6 mg, 0.50 μmol) and H-Ser-Ala-Gln-Lys-Arg-His-Phe-Gly-Ala-SPh (0.5 mg, 0.45 μmol) are mixed in pyridine/acetic acid (50 μl, 1:1, mol/mol). The reaction is stirred at room temperature for 4 hours. Then the solvent is removed by lyophilization. Next, the residue is treated with (TFA/$H_2O$/$Pr_3SiH$, 94/5/1, v/v/v, 0.5 ml, 4 min) at room temperature for 4 min. After the solvent removal by lyophilization, H-Cys(S-t-Bu)-His-Cys(Acm)-Ser-Thr-Cys(Acm)-Tyr-Tyr-His-Lys-Ser-OH (1.1 mg, 0.70 µmol) is added into the same flask containing the crude product from above Ser-NCL, followed by addition of Cys-NCL buffer (pH=7.02, 50 µl). The reaction mixture is stirred at room temperature for 2 hours. The crude reaction mixture is purified by HPLC ($C_4$, 20-30%, MeCN (with 0.04% TFA)/$H_2O$ (with 0.05% TFA), 30 min, flow rate 16 ml/min) to give the three-segment coupled product Fmoc-Arg-Ala-Ser-Ile-Thr-Thr-Ala-Asp-Gly-Ser-Ala-Gln-Lys-Arg-His-Phe-Gly-Ala-Cys-His-Cys(Acm)-Ser-Thr-Cys(Acm)-Tyr-Tyr-His-Lys-Ser-OH (1.0 mg, 60%) (FIG. 7).

The compatibility of unprotected lysine, carboxylic acid, arginine, histidine with aryl thiophenol esters under Ser-NCL condition adds high value to this ligation protocol. The orthogonality between Ser/Thr-NCL with Cys-NCL provides one with a new synthetic strategy towards multiple-segment ligation from the N to the C terminus.

EXAMPLE 7

The method of the present ligation can also be used to prepare cyclic peptides. Model peptide H-Ser-Ala-Gln-Lys-Arg-His-Phe-Gly-Ala-O-salicylaldehyde ester is prepared in a similar manner as described above from Boc-Ser-Ala-Gln(Trt)-Lys(Boc)-Arg(Pbf)-His(Trt)-Phe-Gly-COOH and an alanine salicylaldehyde ester. H-Ser-Ala-Gln-Lys-Arg-His-Phe-Gly-Ala-O-salicylaldehyde ester (0.5 mg, 0.45 µmol) is dissolved in pyridine/acetic acid (5.0 ml, 1:1, mol/mol). The reaction is stirred at room temperature for 10 hours. Then the solvent is removed by lyophilization. Next, the residue is treated with (TFA/$H_2O$/$Pr_3SiH$, 94/5/1, v/v/v, 0.5 ml, 4 min) at room temperature for 4 min. Then the crude reaction mixture is purified by HPLC to give a cyclized peptide (0.3 mg, 67%).

EXAMPLE 8

Other forms of the aryl ester at the C-terminus are evaluated. Fmoc-Ala-OH reacts with 4-hydroxypyridine-3-carboxaldehyde, 2-hydroxy-3-benzafurancarboxaldehyde, 2-formyl-3-hydroxythiophene or 3-hydroxyl-1H-indole-2-carboxaldehyde using dicyclohexylcarbodiimide under standard ester formation conditions to give corresponding aryl ester. Under the same condition as described in EXAMPLE 1, these Fmoc-Ala-aryl esters react with both serine benzyl ester and threonine methyl ester to give corresponding coupled products with an acetal group at the ligation site in good yields (75-90%).

EXAMPLE 9

Except the salicylaldehyde ester being used at the C-terminus, the Fmoc-Ala-salicylaldehyde thioester and Fmoc-Ala-salicylaldehyde selenoester are also explored under the condition of serine/threonine native chemical ligation. They react with serine benzyl ester to give the corresponding coupled N,S-benzylidene acetal product (50%) and N,Se-benzylidene acetal product in 50% and 60% respectively.

The invention claimed is:

1. A method for ligating C-terminal aryl aldehyde ester and N-terminal serine or threonine to chemoselectively produce a natural peptide bond, where said C-terminal aryl aldehyde ester and N-terminal serine or threonine are on the same one starting peptide, or on different starting peptides respectively, said method comprising:
   a) reacting the starting peptide(s) to chemoselectively form an acetal intermediate with an acetal group at the ligation site; and
   b) converting said acetal intermediate to a desired peptide or protein with said natural peptide bond using acid conditions.

2. The method of claim 1, wherein said starting peptide(s) are unprotected starting peptide(s).

3. The method of claim 1, wherein said aryl aldehyde ester has a six-member or five-member aromatic ring.

4. The method of claim 1, wherein said aryl aldehyde ester has a six-member or five-member hetero-aromatic ring, the hetero-atom in the hetero-aromatic ring is at least one atom selecting from N, O, and S.

5. The method of claim 1, wherein said aryl aldehyde ester is a salicylaldehyde ester which has no substituent or has at least one substituent, said acetal group is benzylidene acetal group.

6. The method of claim 1, wherein said acetal intermediate is isolatable and stable.

7. The method of claim 1, wherein said aryl aldehyde ester is O-ester, S-ester or Se-ester.

8. An acetal intermediate, which is obtained by chemoselectively forming acetal group through the reaction of C-terminal aryl aldehyde ester of a first starting peptide and N-terminal serine or threonine of a second starting peptide, said first starting peptide and said second starting peptide are the same one starting peptide, or different starting peptides, said acetal intermediate is able to be converted to a desired peptide or protein with a natural peptide bond using acid conditions.

9. The acetal intermediate of claim 8, wherein said starting peptide(s) are unprotected starting peptide(s).

10. The acetal intermediate of claim 8, wherein said aryl aldehyde ester has a six-member or five-member aromatic ring.

11. The acetal intermediate of claim 8, wherein said aryl aldehyde ester has a six-member or five-member hetero-aromatic ring, the hetero-atom in the hetero-aromatic ring is at least one atom selecting from N, O, and S.

12. The acetal intermediate of claim 8, wherein said aryl aldehyde ester is a salicylaldehyde ester which has no substituent or has at least one substituent, said acetal group is benzylidene acetal group.

13. The acetal intermediate of claim 8, wherein said acetal intermediate is isolatable and stable.

14. The acetal intermediate of claim 8, wherein said aryl aldehyde ester is O-ester, S-ester or Se-ester.

15. A method for a multiple-segment peptide ligation, wherein a first starting peptide, said first starting peptide having a C-terminal aryl aldehyde ester, a second starting peptide, said second starting peptide having a N-terminal serine or threonine and a C-terminal thioester, and a third starting peptide, said third starting peptide having a N-terminal cysteine, react sequentially but in the same pot to produce a three-segment coupled peptide, said method comprising:
   a) reacting the first starting peptide and the second starting peptide to form an acetal intermediate with an acetal group at the ligation site; and
   b) converting said acetal intermediate to a desired peptide or protein with said natural peptide bond using acid conditions.

16. The method of claim 15, wherein said aryl aldehyde ester has a six-member or five-member aromatic ring.

17. The method of claim 15, wherein said aryl aldehyde ester has a six-member or five-member hetero-aromatic ring, the hetero-atom in the hetero-aromatic ring is at least one atom selecting from N, O, and S.

18. The method of claim 15, wherein said aryl aldehyde ester is a salicylaldehyde ester which has no substituent or has at least one substituent.

19. The method of claim 15, wherein said method has no intermediate purification step.

20. The method of claim 15, wherein said method generates two inner amide bonds, as Xaa-Ser/Thr and Xaa-Cys, Xaa is any amino acid.

* * * * *

```
                        SEQUENCE LISTING

<160> NUMBER OF SEQ ID NOS: 17

<210> SEQ ID NO 1
<211> LENGTH: 2
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 1

Ala Ser
1

<210> SEQ ID NO 2
<211> LENGTH: 2
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 2

Val Thr
1

<210> SEQ ID NO 3
<211> LENGTH: 2
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 3

Pro Ser
1
```

```
<210> SEQ ID NO 4
<211> LENGTH: 3
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 4

Val Thr Ser
1

<210> SEQ ID NO 5
<211> LENGTH: 2
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 5

Val Ser
1

<210> SEQ ID NO 6
<211> LENGTH: 2
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 6

Ile Ser
1

<210> SEQ ID NO 7
<211> LENGTH: 3
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 7

Ala Thr Phe
1

<210> SEQ ID NO 8
<211> LENGTH: 3
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 8

Val Thr Phe
1

<210> SEQ ID NO 9
<211> LENGTH: 3
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 9

Pro Thr Phe
1
```

```
<210> SEQ ID NO 10
<211> LENGTH: 3
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 10

Ile Thr Phe
1

<210> SEQ ID NO 11
<211> LENGTH: 4
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 11

Val Thr Thr Phe
1

<210> SEQ ID NO 12
<211> LENGTH: 9
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 12

Arg Ala Ser Ile Thr Thr Ala Asp Gly
1               5

<210> SEQ ID NO 13
<211> LENGTH: 9
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 13

Ser Ala Gln Lys Arg His Phe Gly Ala
1               5

<210> SEQ ID NO 14
<211> LENGTH: 11
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 14

Cys His Cys Ser Thr Cys Thr Thr His Lys Ser
1               5                   10

<210> SEQ ID NO 15
<211> LENGTH: 29
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 15

Arg Ala Ser Ile Thr Thr Ala Asp Gly Ser Ala Gln Lys Arg His Phe
1               5                   10                  15

Gly Ala Cys His Cys Ser Thr Cys Tyr Tyr His Lys Ser
            20                  25
```

```
<210> SEQ ID NO 16
<211> LENGTH: 8
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 16

Ser Ala Gln Lys Arg His Phe Gly
1               5

<210> SEQ ID NO 17
<211> LENGTH: 9
<212> TYPE: PRT
<213> ORGANISM: Artificial Sequence
<220> FEATURE:
<223> OTHER INFORMATION: SYNTHETIC FROM PEPTIDE COUPLING METHOD

<400> SEQUENCE: 17

Ser Ala Gln Lys Arg His Phe Gly Ala
1               5
```